(12) United States Patent
Peeters

(10) Patent No.: US 6,217,751 B1
(45) Date of Patent: Apr. 17, 2001

(54) WATER QUALITY MONITOR FOR A REVERSE OSMOSIS WATER PURIFICATION SYSTEM

(75) Inventor: Brad Peeters, Costa Mesa, CA (US)

(73) Assignee: Aquatec Water Systems, Inc., Irvine, CA (US)

( * ) Notice: Subject to any disclaimer, the term of this patent is extended or adjusted under 35 U.S.C. 154(b) by 0 days.

(21) Appl. No.: 08/377,776

(22) Filed: Jan. 23, 1995

(51) Int. Cl.$^7$ ................................................. B01D 17/12
(52) U.S. Cl. ........................... 210/85; 210/96.1; 324/439; 324/443; 340/603
(58) Field of Search ................... 210/85, 96.1, 96.2; 310/603; 324/439, 442, 443

(56) References Cited

U.S. PATENT DOCUMENTS

| | | | |
|---|---|---|---|
| 3,838,774 | * 10/1974 | Dolan et al. | 210/96.2 |
| 3,990,066 | * 11/1976 | Malmgren | 210/96.2 |
| 4,201,085 | 5/1980 | Larson . | |
| 4,806,912 | * 2/1989 | Clack | 324/442 |
| 4,847,598 | * 7/1989 | Tucci et al. | 210/96.1 |
| 4,851,818 | 7/1989 | Brown et al. | 340/603 |
| 4,937,557 | * 6/1990 | Tucci et al. | 210/96.2 |
| 5,004,535 | 4/1991 | Bosko et al. | 210/90 |
| 5,057,212 | 10/1991 | Burrows . | |
| 5,096,574 | * 3/1992 | Birdsong et al. | 210/96.2 |

* cited by examiner

Primary Examiner—Joseph W. Drodge
(74) Attorney, Agent, or Firm—Irell & Manella LLP

(57) ABSTRACT

A water conductivity monitor that is controlled by a microcontroller which provides a pair of probe driving signals that are 180° out of phase. The monitor is connected to a feed water probe that is located within the unfiltered water of a water purification system and a filter water probe that is located within the filtered water of the system. The driving signals are provided to the probes to create a probe test signal. The filtered water test signal is a ratio of the voltage across the feed water probe and the voltage across the filter water probe. The driving signals are also provided to a resistor circuit which provides a threshold test signal. The test signals are integrated by an integrator circuit which is controlled by the microcontroller. The integrated test signals are compared by a comparator. The comparator provides an output signal to the microcontroller if the voltage level of the probe test signal is below the threshold test signal. The output signal is indicative of an unacceptable filtered water conductivity. The microcontroller illuminates an indicator light if the controller counts a predetermined number of output signals.

14 Claims, 2 Drawing Sheets

WATER QUALITY MONITOR FOR A REVERSE OSMOSIS WATER PURIFICATION SYSTEM

BACKGROUND OF THE INVENTION

1. Field of the Invention

The present invention relates to a monitor that tests the conductivity of water.

2. Description of Related Art

Municipal water can contain an unacceptable amount of impurities. Some end users use a reverse osmosis (RO) purification unit to remove the impurities from the water. RO units contain a membrane that captures the impurities while allowing "filtered" water to flow therethrough. Additionally, RO water purification systems may also include a pre-membrane filter and possibly a post-membrane filter to further purify the water. Over time the RO membrane and filters become less effective in removing contaminants from the water. If this condition is not detected and corrected by the replacement of the membrane and/or filter, the water purification unit will become inefficient and the quality of water will decrease to an unacceptable level. It is therefore desirable to have a sensor that can monitor the quality of water in a water purification unit.

U.S. Pat. No. 5,057,212 issued to Burrows discloses a water conductivity monitor for a water purification system. The purification system has a feed water probe within the unfiltered water and a filter water probe within the filtered water of the system. The Burrows monitor includes a button that is coupled to a battery and which provides a voltage to the probes when depressed by an end user. A comparator compares the ratio of the feed water probe voltage and filter water probe voltage, with a threshold value to determine whether the conductivity of the filtered water is below an acceptable level. The output of the comparator is latched into a light emitting diode (LED) to provide an indication of whether the water "passed" or "failed" the test.

The battery in the Burrows monitor is a DC voltage source which will induce electrolysis between the metal surfaces of the probes. Additionally, the probes will function as capacitors that store energy and distort the results of the test. To reduce the "battery" effect of the probes, the Burrows monitor includes a capacitor that creates a reverse flow of current through the probes. Unfortunately electrolysis of the probes still occurs. It would be desirable to provide a water conductivity monitor that does not have the disadvantages of the prior art.

SUMMARY OF THE INVENTION

The present invention is a water conductivity monitor that is controlled by a microcontroller which provides a pair of probe driving signals that are 180° out of phase. The monitor is connected to a feed water probe that is located within the unfiltered water of a water purification system and a filter water probe that is located within the filtered water of the system. The driving signals are provided to the probes to create a probe test signal. The filtered water test signal is a ratio of the voltage across the feed water probe and the voltage across the filter water probe. The driving signals are also provided to a resistor circuit which provides a threshold test signal. The test signals are integrated by an integrator circuit which is controlled by the microcontroller. The integrated test signals are compared by a comparator. The comparator provides an output signal to the microcontroller if the voltage level of the probe test signal is above the threshold test signal. The output signal is indicative of an unacceptable filtered water conductivity. The microcontroller illuminates an indicator light if the controller counts a predetermined number of output signals.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
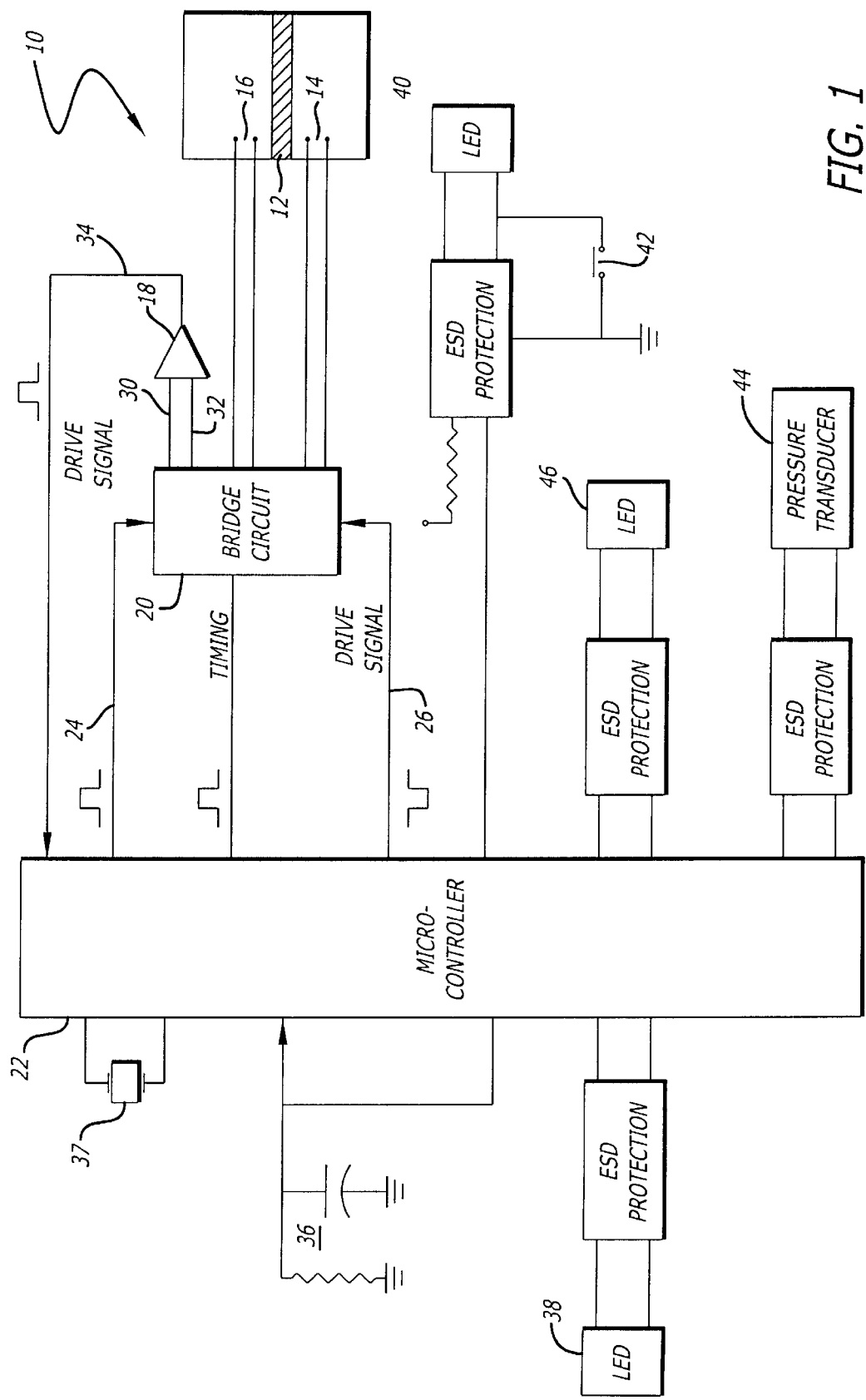
FIG. 1 is a schematic of a water conductivity monitor of a water purification system.

Referring to the drawings more particularly by reference numbers, FIG. 1 shows a water purification system 10. The system 10 has a filter 12 that purifies water flowing therethrough. Although a filter 12 is described, it is to be understood that the device 12 may be any other type of water purification element such as a reverse osmosis membrane. Upstream from the filter 12 is unfiltered feed water. Downstream from the device is filtered water.

Located within the feed water is a feed water probe 14. Located within the filtered water is a filter water probe 16. Each probe 14 and 16 typically contains a pair of separated electrodes that allow water to flow therethrough. The electrodes are utilized to measure the electrical resistance of the water. It being understood that the resistance of the water increases with the purity of the water. A water resistance of a sufficiently high value is generally indicative of an acceptable water purity level.

The probes 14 and 16 are coupled to a comparator 18 by a bridge circuit 20. The bridge circuit 20 and probes receive driving signals from a microcontroller 22 on lines 24 and 26. The bridge circuit 20 produces a threshold test signal and a probe test signal in response to the driving signals. The threshold test signal and probe test signal are provided to the inputs of the comparator 18 on lines 30 and 32. If the probe test signal is above the threshold test signal, the comparator 18 will provide an output signal to the microcontroller 22 on line 34. The generation of an output signal may be indicative of a "failed" condition, whereas the absence of an output signal may be indicative of a "pass" condition.

The controller 22 will generate the driving signals within a "sample" period. During the sample period the microcontroller 22 will generate a plurality of driving signals and sense the output signal line 34 to determine the condition of the water. The sample period is repeated periodically within a sample cycle. The sample cycle is typically set by an RC circuit 36 attached to the microcontroller 22. The RC circuit 36 can be varied by the manufacturer to provide different sampling cycles. For example, the sampling cycle may range from 15 seconds to 15 minutes between each sampling period. The system typically has an oscillator 37 that is connected to the controller 22.

The controller 22 can be coupled to a bicolor light emitting diode (LED) 38 that is illuminated a first color (e.g. green) to provide a pass indication, and is illuminated a second color (e.g. red) to provide a failed indication. The microcontroller 22 may be programmed to illuminate the LED 38 red only when the comparator 18 generates a predetermined number of consecutive output signals. For example, the microcontroller 22 may illuminate the LED 38 red only after receiving 4 consecutive output signals from the comparator 28. Requiring a number of consecutive output signals prevents a momentary system aberration from generating an indication that the filter 12 requires service.

The controller 22 may also be programmed to illuminate LED 40 after a predetermined time period. For example, the LED 40 can be illuminated after a one year time period to provide an indication that the filter 12 may require service. The system may have a reset switch 42 that can be depressed by the end user to turn off the LED 40. The LED 40 may provide a general reminder to the end user that it has been a certain time period (e.g. one year) since the filter 12 was last serviced.

The controller 22 may also be coupled to a pressure transducer 44 that provides a feedback signal that corresponds to the pressure drop across the filter. The controller 22 may illuminate LED 46 in response to an input signal from the transducer 44 to provide an indication that the filter may need service. The transducer 44 may be a simple pressure switch that closes when the output pressure of the filter falls below a set value.

Figure 2:
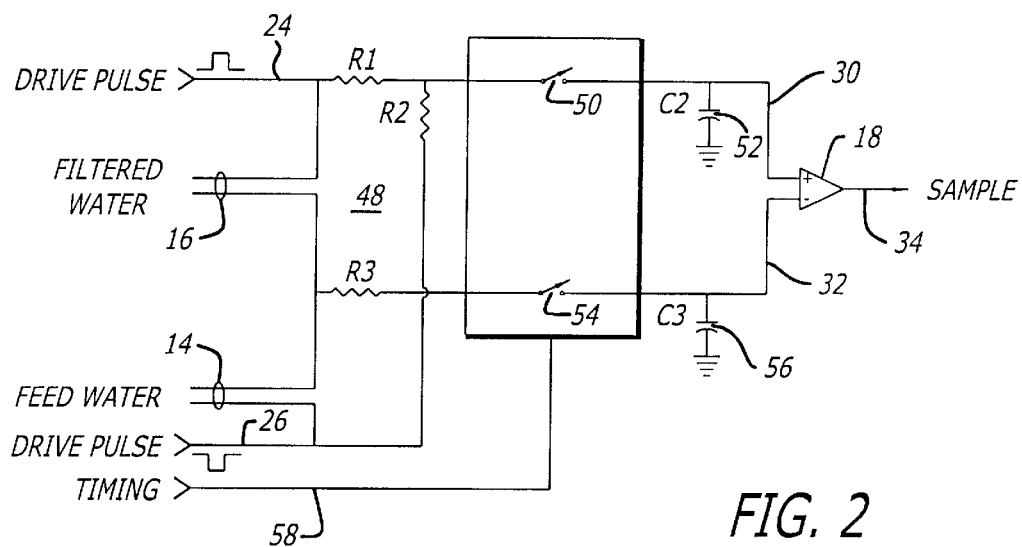
FIG. 2 is a schematic of a bridge circuit of the monitor.

FIG. 2 shows a preferred embodiment of the bridge circuit 20. The probes 14 and 16 are connected to the driving signal lines 24 and 26. The controller 22 provides a first square wave driving signal on line 24 and a second square wave driving signal on line 26. The driving signals are 180° out of phase. The driving signals collectively provide an alternating current which reduces the electrolytic battery effects on the probes 14 and 16. The dual driving signals allow the probes 14 and 16 to be tested with a conventional DC logic power level such as 5 volts, allowing the monitor to be readily integrated within a digital electronic system.

A resistor circuit 48 containing resistors R1 and R2 provides a series of threshold test signals in response to the driving signals. The resistance values of the circuit are set to create a threshold test signal that defines a threshold value for the conductivity of the water. Resistor R3 is connected to the midpoint of the probes 14 and 16. The probes and resistor R3 provide a series of probe test signals in response to the driving signals. The probe test signals represent a ratio between the voltage across the feed water probes 14 and the voltage across the filter water probes 16.

Figure 3:
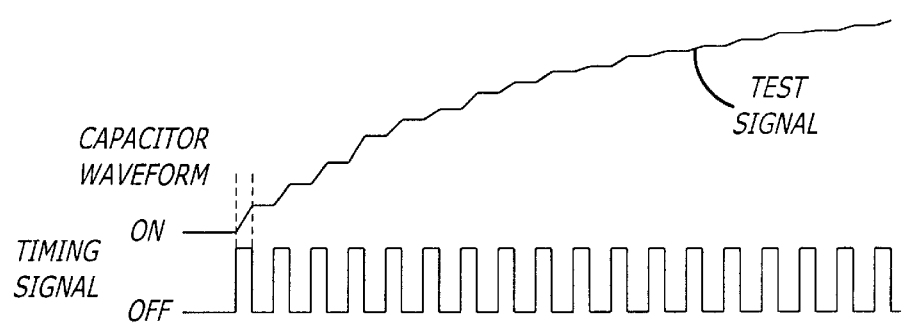
FIG. 3 is a graph showing an integrated waveform.

The resistor circuit 48 is coupled to the input line 30 of the comparator 18 by a first switch 50 and a first capacitor 52. The resistor R3 is coupled to the other comparator input line 32 by a second switch 54 and a second capacitor 56. The switches 50 and 54 are typically within a single integrated circuit and controlled by a timing signal provided from the controller 22 on line 58. The controller 22 opens and closes the switches 50 and 54 to integrate the test signals provided to the comparator. The switches are typically turned on when the controller 22 provides the positive driving signal on line 24 and turned off when the controller 22 provides the negative driving signal on line 24. As shown in FIG. 3, the charging and discharging constants of the bridge circuit 20 can be set to create an integrated waveform that reaches a peak value within the sample period of the system. The controller 22 senses the output of the comparator 18 when the test signals reach the peak voltage value.

In operation, the controller 22 will initiate a test sample by generating a plurality of driving signals that are provided to the bridge circuit 20. Test signals are created in response to the driving signals. The test signals are then integrated and compared by the comparator 18. If the probe test signal is above the threshold test signal the comparator 18 will provide an output signal that is counted by the controller 22. The controller 22 will periodically repeat the test sample to sense the conductivity of the water. If a predetermined number of consecutive output signals are counted, the controller 22 will illuminate the LED 38 red, otherwise the LED 38 is illuminated green. To save power within the system, the controller 22 may be programmed to discontinue further sampling if a predetermined number of output signals have been counted and the LED 38 is illuminated red.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A water conductivity monitor that is connected to a filter probe and a feed water probe, comprising:

a resistor circuit;

a microcontroller that generates a plurality of first drive pulses, and a plurality of second drive pulses that are 180° out of phase from said first drive pulses, wherein said first and second drive pulses are sequentially provided to both the filter probe and the feed water probe, and provided to said resistor circuit to create a plurality of probe test signals and a plurality of threshold test signals; and, a comparator that compares said probe test signals and said threshold test signals and provides an output signal to said microcontroller.

2. The monitor as recited in claim 1, further comprising an integrator circuit that integrates said probe test signals and said threshold test signals.

3. The monitor as recited in claim 2, wherein said integrator circuit includes a first switch and a first capacitor that integrate said probe test signals, and a second switch and a second capacitor that integrate said threshold test signals.

4. The monitor as recited in claim 3, wherein said first and second switches are controlled by said microcontroller.

5. A water conductivity monitor that is connected to a filter probe and a feed water probe, comprising:

a resistor circuit;

a microcontroller that generates a plurality of first drive pulses that are provided to the filter and feed water probes, and said resistor circuit, to create a plurality of probe test signals and a plurality of threshold test signals;

an integrator circuit that integrates said probe test signals and said threshold test signals; and, a comparator that compares said integrated probe test signals and said integrated threshold test signals and provides an output signal to said microcontroller.

6. The monitor as recited in claim 5, wherein said integrator circuit includes a first switch and a first capacitor that integrate said probe test signals, and a second switch and a second capacitor that integrate said threshold test signals.

7. The monitor as recited in claim 6, wherein said first and second switches are controlled by said microcontroller.

8. A water conductivity monitor that is connected to a filter probe and a feed water probe, comprising:

a resistor circuit;

microcontroller means for generating a plurality of first drive pulses and a plurality of second drive pulses that are 180° out of phase from said first drive pulses, wherein said first and second drive pulses are sequentially provided to both the filter probe and the feed water probe, and provided to said resistor circuit to create a plurality of probe test signals and a plurality of threshold test signals; and, comparator means for comparing said probe test signals and said threshold test signals and providing an output signal to said microcontroller means.

9. The monitor as recited in claim 8, further comprising integrator means for integrating said probe test signals and said threshold test signals.

10. The monitor as recited in claim 9, wherein said integrator means includes a first switch and a first capacitor that integrate said probe test signals, and a second switch and a second capacitor that integrate said threshold test signals.

11. The monitor as recited in claim 10, wherein said first and second switches are controlled by said microcontroller means.

12. A water conductivity monitor that is connected to a filter probe and a feed water probe, comprising:

a resistor circuit;

microcontroller means for generating a plurality of first drive pulses that are provided to the filter and feed water probes, and said resistor circuit, to create a plurality of probe test signals and a plurality of threshold test signals;

integrator means for integrating said probe test signals and said threshold test signals; and, comparator means for comparing said integrated probe test signals and said integrated threshold test signals and providing an output signal to said microcontroller means.

13. The monitor as recited in claim 12, wherein said integrator means includes a first switch and a first capacitor that integrate said probe test signals, and a second switch and a second capacitor that integrate said threshold test signals.

14. The monitor as recited in claim 13, wherein said first and second switches are controlled by said microcontroller means.

* * * * *